United States Patent
Balandras et al.

(10) Patent No.: US 8,530,423 B2
(45) Date of Patent: *Sep. 10, 2013

(54) ANXIOLYTIC COMPOSITIONS CONTAINING $\alpha_{s1}$-CASEIN-DERIVED PEPTIDES

(75) Inventors: Federique Balandras, Nancy (FR);
Jean-Luc Gaillard, Luc sur Mer (FR);
Francois Laurent, Nancy (FR); Yves Le Roux, Vandoeuvre-les-Nancy (FR);
Laurent Miclo, Villers-les-Nancy (FR)

(73) Assignee: Universite de Lorraine, Nancy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/996,506

(22) PCT Filed: Jun. 5, 2009

(86) PCT No.: PCT/EP2009/056933
§ 371 (c)(1),
(2), (4) Date: Mar. 14, 2011

(87) PCT Pub. No.: WO2009/147234
PCT Pub. Date: Dec. 10, 2009

(65) Prior Publication Data
US 2011/0312892 A1  Dec. 22, 2011

(30) Foreign Application Priority Data
Jun. 6, 2008  (FR) ..................... 08 53757

(51) Int. Cl.
*A01N 37/18* (2006.01)
*A61K 38/00* (2006.01)

(52) U.S. Cl.
USPC ....... 514/17.5; 514/17.6; 514/17.7; 514/21.8; 435/69.1

(58) Field of Classification Search
None
See application file for complete search history.

(56) References Cited

U.S. PATENT DOCUMENTS 5,846,939 A * 12/1998 Miclo et al. .................. 514/17.5
6,465,432 B1 * 10/2002 Han et al. ...................... 514/5.5

FOREIGN PATENT DOCUMENTS

| EP | 0714910 A | 6/1996 |
|---|---|---|
| EP | 1188767 A1 | 3/2002 |
| WO | 2009/147234 A3 | 12/2009 |

OTHER PUBLICATIONS

Loukas et al., Biochem., 1983, 22:4567-73.*
Miclo et al., FASEB, 2001, 15:1780-2.*
Mercier, J.C., Grosclaude, F., and Ribadeau-Dumas, B., 1971, Structure primaire de la caseine αs1 bovine. Sequence complete. Eur. J. Biochem., 23, 41-51.
Nagao, M., Maki, M., Sasaki, R., and Chiba, H., 1984, Isolation and sequence analysis of bovine as1-casein cDNA clone. Agric. Biol. Chem., 48, 1663-1667.
Zioudrou, C., Streaty, R.A., and Klee, W.A., 1979, Opioid peptides derived from food proteins: the exorophins, J. Biol. Chem., 254, 2446-2449.
Maruyama, S., and Suzuki, H., 1982. A peptide inhibitor of angiotensin I converting enzyme in the tryptic hydrolysate of casein. Agric. Biol. Chem., 46, 1393-1394.
Maruyama, S., Mitachi, H., Awaya, J., Kurono, M., Tomizuka, N., and Suzuki, H., 1987, Angiotensin I-converting enzyme inhibitory activity of the C-terminal hexapeptide of as1-casein: Agric. Biol. Chem., 51, 2557-2561.
Lecouvey, M., Frochot, C., Miclo, L., Orlewski, P., Driou, A., Linden, A., Gaillard, J.L., Marraud, M., Cung, M.T. and Vanderesse, R., 1997, Two dimensional 1H-NMR and CD structural analysis in a micellar medium of a bovine as1-casein fragment having benzodiazepine-like properties. Eur. J. Biochem., 248, 872-878.
Maubois, J.L., 1984. Separation, extraction and fractionation of milk protein components, Lait, 64, 485-495.
Sanogo, ET., Paquet, D., Aubert, F., and Linden, G., 1989, Purification of as1-casein by Fast Protein Liquid Chromatography. J. Dairy Sci., 72, 2242-2246.
Merrifield, R.B., 1963, Solid phase peptide synthesis. I. Synthesis of a tetrapeptide. J. Am. Chem. Soc., 85, 2149-2154.
Bourin, M., and Hascoet, M., 2003, The mouse light/dark box test. Eur. J. Pharmaco., 463, 55-65.

* cited by examiner

*Primary Examiner* — Olga N Chernyshev
(74) *Attorney, Agent, or Firm* — McCarter & English, LLP

(57) ABSTRACT

The invention relates to pharmaceutical compositions and food products containing peptides derived from the $\alpha_{s1}$-casein in milk and having benzodiazepine-type activity and particularly, anxiolytic activity.

12 Claims, 2 Drawing Sheets

SEQUENCE LISTING

<160> NUMBER OF SEQ ID NOS: 2

<210> SEQ ID NO 1
<211> LENGTH: 5
<212> TYPE: PRT
<213> ORGANISM: Bos taurus

<400> SEQUENCE: 1

Tyr Leu Gly Tyr Leu
1               5

<210> SEQ ID NO 2
<211> LENGTH: 6

-continued

```
<212> TYPE: PRT
<213> ORGANISM: Bos taurus

<400> SEQUENCE: 2

Tyr Leu Gly Tyr Leu Glu
1               5
```

ANXIOLYTIC COMPOSITIONS CONTAINING $\alpha_{s1}$-CASEIN-DERIVED PEPTIDES

Figure 1:
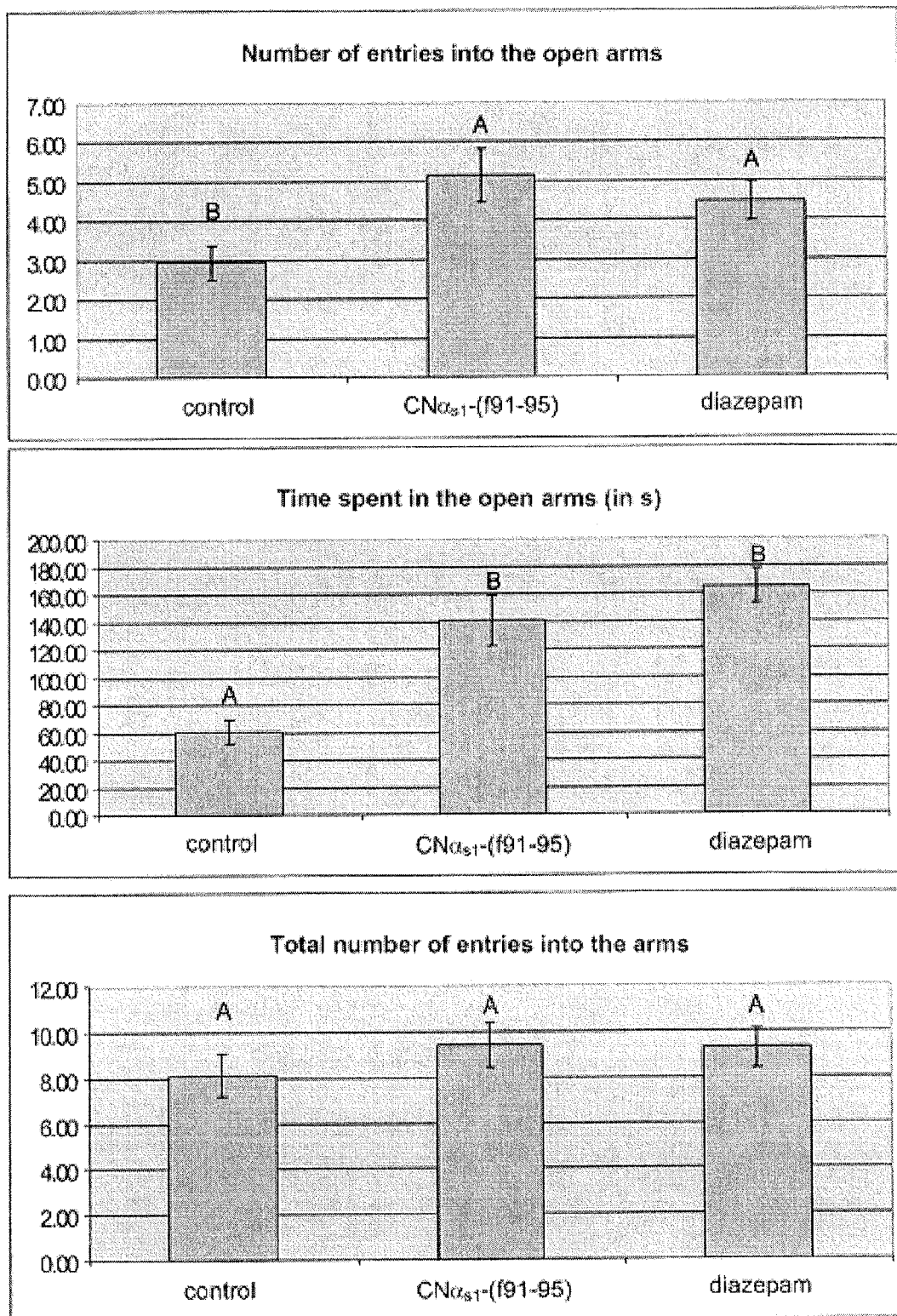

This invention relates to pharmaceutical compositions and food compositions including $\alpha_{s1}$ casein-derived peptides having an anxiolytic activity.

Casein yields, by different fractionation techniques, the main fractions respectively called: K-casein, β-casein, $\alpha_{s1}$-casein and $\alpha_{s2}$-casein. The amino acid sequences of these caseins are well known, in particular that of $\alpha_{s1}$-casein has been determined by MERCIER et al. (1) and NAGAO et al. (2).

It has been demonstrated that certain peptide fragments of these different caseins have diverse biological activities and in particular opiate or anti-opiate activities and angiotensin-I converting enzyme inhibitor activities. Thus, $\alpha_{s1}$-casein peptides 90-96 and 90-95 have a demonstrated in vitro opiate activity [ZIOUDROU et al. (3) and LOUKAS et al. (4)]. The arginine residue in position 90 appears to be important for this opiate activity. Peptides 91-95 and 91-96 in which the arginine residue is suppressed are practically inactive and therefore have a much lower opiate activity than peptide 90-96. Peptides 23-24 and 194-199 are angiotensin-I converting enzyme inhibitors [MARUYAMA and SUZUKI (5) and MARUYAMA et al, (6)].

A peptide having an original anxiolytic activity was identified in an $\alpha_{s1}$-casein tryptic hydrolysate [EP 0714910 (7)]. It corresponds to fragment 91-100 and was named α-casozepine [MICLO et al. (8)]. Guesdon et al, (18) also showed that this same tryptic hydrolysate of casein including peptide 91-100 improves sleep in rats subjected to chronic stress. The structure of this decapeptide was studied by two-dimensional $^1$H-NMR. The sequence contained between the glycine 93 and leucine 99 residues adopts, in a micellar medium, a $3_{10}$ helical structure initiated and terminated by an α helix. The lateral chains of the hydrophobic residues are located on the same face of the helix, while the lateral chains of the hydrophilic residues are located on the other face, thereby conferring an amphiphilic character on the peptide and enabling it to interact with membranes. The ionic interactions between the guanidinium group of the arginine 100 residue and the carboxylic groups of the glutamic acid 96 and arginine 100 residues show the critical role of the carboxy-terminal arginine residue in the stabilization of the helical structure. In such a structure, the aromatic rings of the two tyrosine residues in position 91 and 94 are oriented so that the distance between their center (0.56 nm on average) is comparable to the distance observed between the centers of the aromatic rings of nitrazepam, a benzodiazepine known for its anxiolytic properties [LECOUVEY et al. (9)]. The substitution of the arginine 100 residue with an alanine residue significantly decreases the helicity of the decapeptide and results in a decrease in the affinity of this peptide for the benzodiazepine site of the $GABA_A$ receptor by a factor of 300,000 [Thesis of Céline Frochot, (10)]. This decapeptide, after oral absorption, may be subject to proteolytic attacks by digestive tract enzymes, which can reduce the bioavailability thereof and consequently prevent it from reaching its biological target. However, it is well known for small peptides that the enterocyte absorption is more effective than that of larger fragments and that their resistance to digestive proteases is increased. Thus, among the fragments generated during digestion of the decapeptide, some may be more absorbable and more resistant, but in view of the structural data of the decapeptide, incapable of preserving the slightest anxiolytic activity.

The pending patent application PCT/EP2007/063863 surprisingly shows that peptides 91-97, 91-98 and 91-99 derived from decapeptide and not containing the key arginine 100 residue show anxiolytic properties in in vivo behavioral tests in the rat. In view of their small size, these peptides are more easily absorbable and less easily degradable.

This application will now discuss the pharmaceutical compositions and food products having anxiolytic properties including peptides 91-95 and 91-96 derived from $\alpha_{s1}$-casein. It was possible to demonstrate the anxiolytic properties of these peptides in in vivo behavioral tests in the rat.

SEQUENCE LISTING

SEQ ID No. 1: Pentapeptide corresponding to positions 91-95 of $\alpha_{s1}$-casein SEQ ID No. 2: Hexapeptide corresponding to positions 91-96 of $\alpha_{s1}$-casein

DESCRIPTION OF THE INVENTION

The invention relates to pharmaceutical compositions including, as an active principle, an effective amount of a peptide according to SEQ ID No. 1 and/or a peptide according to SEQ ID No. 2 in combination with a suitable pharmaceutical vehicle.

The pharmaceutical compositions according to the invention have a benzodiazepine action and are more specifically suitable for treating anxiety, sleep disorders and epilepsy.

In a specific embodiment, the invention relates to pharmaceutical compositions including a hydrolysate or a fraction of a hydrolysate of casein or $\alpha_{s1}$-casein, containing an effective amount of a peptide according to SEQ ID No. 1 and/or a peptide according to SEQ ID No. 2.

The invention also relates to a food product for people subject in particular to anxiety, sleep disorders and/or epilepsy including an effective amount of at least one peptide according to SEQ ID No. 1 and/or SEQ ID No 2.

In an advantageous embodiment of the invention, the food product includes a hydrolysate or a fraction of a hydrolysate of casein or $\alpha_{s1}$-casein, containing an effective amount of a peptide according to SEQ ID No. 1 and/or a peptide according to SEQ ID No. 2.

The invention also relates to isolated polynucleotides coding for a peptide according to SEQ ID No. 1 or for a peptide according to SEQ ID No. 2.

The invention also relates to expression vectors including a polynucleotide according to the invention.

The invention also relates to a host organism, excluding humans, transformed with a polynucleotide according to the invention and/or with an expression vector according to the invention.

The invention also relates to a transformed host organism, excluding humans, expressing a peptide according to SEQ ID No. 1 or a peptide according to SEQ ID No. 2.

The invention also relates to the use of a peptide according to SEQ ID No. 1, a peptide according to SEQ ID No. 2, a polynucleotide according to the invention, an expression vector according to the invention and/or a host organism according to the invention for the production of a drug for treating anxiety, sleep disorders and epilepsy.

Preferably, the invention relates to the use of a hydrolysate of casein or $\alpha_{s1}$-casein and/or a fraction of a hydrolysate of casein or $\alpha_{s1}$-casein, containing an effective amount of a peptide according to SEQ ID No. 1 and/or a peptide according to SEQ ID No. 2 for the production of a drug for treating anxiety, sleep disorders and epilepsy.

Preferably, the drug has a benzodiazepine-type activity.

The invention also relates to the use of a peptide according to SEQ ID No. 1, a peptide according to SEQ ID No. 2, a polynucleotide according to the invention, an expression vector according to the invention and/or a host organism according to the invention for the production of a food product for people susceptible in particular to anxiety, sleep disorders and/or epilepsy.

Preferably, the invention relates to the use of a hydrolysate of casein or $\alpha_{s1}$-casein and/or a fraction of a hydrolysate of casein or $\alpha_{s1}$-casein, containing an effective amount of a peptide according to SEQ ID No. 1 and/or a peptide according to SEQ ID No. 2 for the production of a food product for people susceptible in particular to anxiety, sleep disorders and/or epilepsy.

Thus, this invention relates to pharmaceutical compositions and food products including $\alpha_{s1}$-casein-derived peptides of which the sequence is represented in SEQ ID Nos: 1 and 2. The invention therefore relates to pharmaceutical compositions and food products containing peptides of which the amino acid sequence is chosen from: Tyr-Leu-Gly-Tyr-Leu identified by SEQ ID No: 1, and Tyr-Leu-Gly-Tyr-Leu-Glu identified by SEQ ID No: 2.

The invention also relates to pharmaceutical compositions and food products including modified peptides having one of SEQ ID Nos. 1 or 2 and preserving their anxiolytic properties. The invention also relates to pharmaceutical compositions and food products including fusion proteins or recombinant proteins including the peptides according to SEQ ID No. 1 and/or SEQ ID No. 2.

In a second aspect, the invention relates to polynucleotides coding for the peptides according to SEQ ID No. 1 and SEQ ID No. 2. Due to the degeneration of the genetic code, different polynucleotides may code for the same peptide. According to this invention, by "polynucleotide", we mean a single-strand nucleotide chain or the complementary thereof capable of being DNA or RNA, or a double-strand nucleotide chain capable of being cDNA (complementary) or genomic. Preferably, the polynucleotides of the invention are DNA, in particular double-strand DNA. The term "polynucleotide" also refers to modified polynucleotides. Preferably, the polynucleotides of this invention can be prepared by conventional molecular biology techniques as described by Sambrook et al. (Molecular Cloning: A Laboratory Manual, 1989) or by chemical synthesis.

The invention also relates to a host organism expressing a peptide according to one of SEQ ID Nos. 1 or 2. The peptides according to SEQ ID No. 1 and SEQ ID No. 2 can be expressed and produced in different host organisms according to techniques well known to a person skilled in the art. Typically, the host organism is transformed with an expression cassette including a polynucleotide coding for a peptide according to SEQ ID No. 1 or SEQ ID No. 2. This polynucleotide can be integrated in the genome of the host organism or be replicated in a stable manner in the host organism. By host organism, we mean in particular according to the invention any low or high single- or multi-cell organism, in particular chosen from bacteria, yeast, fungus and mammals. By host organism, we mean a non-human organism. The peptides according to SEQ ID No. 1 or SEQ ID No. 2 can therefore be produced, then isolated or purified from transformed host organisms expressing them.

Preferably, the peptides according to SEQ ID No. 1 or SEQ ID No. 2 are obtained from milk casein or more preferably from $\alpha_{s1}$-casein. The casein used is preferably bovine milk casein and more preferably cow's milk casein (Bos taurus). The sequence of the $\alpha_{s1}$-casein is referenced in the Swiss Prot database under number P02662. After fractionation of the milk proteins, the casein is "digested" or hydrolyzed with suitable enzymes in order to obtain the peptides according to the invention. In a first embodiment, the milk casein is hydrolyzed directly with enzymes in order to obtain the desired peptides. In this embodiment, it may be necessary to partially or totally purify the peptides according to SEQ ID No. 1 or SEQ ID No. 2 after hydrolysis. In a second embodiment according to the invention, the enzymatic hydrolysis is performed directly on the $\alpha_{s1}$-casein. In this embodiment, the hydrolysate obtained will already be enriched with peptides according to SEQ ID No. 1 or SEQ ID No. 2, and additional purification steps are often unnecessary. A person skilled in the art will choose the suitable enzymes for obtaining the desired peptides. These techniques are well known to a person skilled in the art and described in the literature. The invention therefore also relates to a casein hydrolysate including a peptide according to SEQ ID No. 1 or SEQ ID No. 2. Preferably, it is a $\alpha_{s1}$-casein hydrolysate.

The pharmaceutical compositions and food products according to this invention have a benzodiazepine-type activity and in particular an anxiolytic effect.

The invention relates to pharmaceutical compositions having a benzodiazepine-type activity in particular for the treatment of anxiety, sleep disorders and epilepsy.

The invention therefore also relates to pharmaceutical compositions containing, as an active principle, an effective amount of a peptide according to SEQ ID No. 1 and/or a peptide according to SEQ ID No. 2 in combination with a suitable pharmaceutical vehicle.

These compositions can be formulated for administration to mammals, including humans. The dosage varies according to the treatment and according to the condition to be treated. These compositions are produced so as to be suitable for digestive or parenteral administration.

In the pharmaceutical compositions of the present invention for oral, sublingual, subcutaneous, intramuscular, intravenous, transdermal, local or rectal administration, the active ingredient can be administered in unitary administration forms, in a mixture with conventional pharmaceutical carriers, to animals or human beings. The suitable unitary administration forms include oral forms such as tablets, gel caps, powders, granules or oral solutions or suspensions, sublingual and oral administration forms, subcutaneous, intramuscular, intravenous, intranasal or intraocular administration forms and rectal administration forms.

When a solid composition is prepared in the form of tablets, the active principle ingredient is mixed with a pharmaceutical vehicle such as gelatin, starch, lactose, magnesium stearate, talc, gum arabic or the like. The tablets can be coated with sucrose or other suitable materials or they can be treated so as to have a prolonged or delayed activity and so as to continuously release a predetermined amount of active principle.

A gel cap preparation is obtained by mixing the active ingredient with a diluent and by pouring the mixture obtained into soft or hard gel caps.

A preparation in the form of a syrup or an elixir can contain the active ingredient in combination with a sweetener, an antiseptic, as well as a flavoring agent and a suitable coloring agent.

The powders or granules dispersible in water can contain the active ingredient in a mixture with dispersion agents or wetting agents, or agents in suspension, as well as with flavor correctors or sweeteners.

The compositions according to the invention can be used in treatment alone or in combination with at least one other active agent. These other active agents are in particular chosen from the active agents suitable for the treatment of anxiety, sleep disorders and epilepsy. These may be adjuvants enabling the activity of the compounds according to the invention to be enhanced, or other active agents known for their use in the treatment of said conditions. Such active agents are well known to a person skilled in the art, available on the market or are described in reference works such as Le Dictionnaire Vidal, published in new editions each year.

This invention therefore also relates to pharmaceutical composition including a peptide according to SEQ ID No. 1 and/or a peptide according to SEQ ID No. 2, as well as another active agent as a combination product for simultaneous use, separate use or for use spread out over time in treatments, in particular for anxiety and sleep disorders. These other active agents are chosen in particular from the active agents suitable for the treatment of anxiety, such as, for example, the compounds of the benzodiazepines class or serotonin reuptake inhibitors.

The invention also relates to the use of a peptide according to SEQ ID No. 1, a peptide according to SEQ ID No. 2, a polynucleotide according to the invention, an expression vector according to the invention and/or a host organism according to the invention for the production of a drug for treating anxiety, sleep disorders and epilepsy.

Preferably, the invention relates to the use of a hydrolysate of casein or $\alpha_{s1}$-casein and/or a fraction of a hydrolysate of casein or $\alpha_{s1}$-casein, containing an effective amount of a peptide according to SEQ ID No. 1 and/or a peptide according to SEQ ID No. 2 for the production of a drug for treating anxiety, sleep disorders and epilepsy.

The invention also relates to methods for therapeutic treatment of anxiety, sleep disorders and epilepsy including the administration to an individual of an effective amount of a peptide according to SEQ ID No. 1, a peptide according to SEQ ID No. 2, a polynucleotide according to the invention, an expression vector according to the invention and/or a host organism according to the invention.

The invention also relates to methods for therapeutic treatment of anxiety, sleep disorders and epilepsy including the administration to an individual of a hydrolysate of casein or $\alpha_{s1}$-casein and/or a fraction of a hydrolysate of casein or $\alpha_{s1}$-casein, containing an effective amount of a peptide according to SEQ ID No. 1 and/or a peptide according to SEQ ID No. 2.

The invention also relates to the use of a peptide according to SEQ ID No. 1, a peptide according to SEQ ID No. 2, a polynucleotide according the invention, an expression vector according to the invention and/or a host organism according to the invention for the production of a food product for people susceptible in particular to anxiety, sleep disorders and/or epilepsy.

Preferably, the invention relates to the use of a hydrolysate of casein or $\alpha_{s1}$-casein and/or a fraction of a hydrolysate of casein or $\alpha_{s1}$-casein, containing an effective amount of a peptide according to SEQ ID No. 1 and/or a peptide according to SEQ ID No. 2 for the production of a food product for people susceptible in particular to anxiety, sleep disorders and/or epilepsy.

By food product, we mean anything capable of serving as a food. The peptides of SEQ ID No. 1 and SEQ ID No. 2 can be used as an active principle in food products in combination with protein, carbohydrate or fatty food supports, in food products intended for a particular type of nutrition. The food products of this invention can also be in the form of food supplements. These food supplements are suitable for supplementing the diet of people susceptible in particular to anxiety, sleep disorders and epilepsy.

The invention also relates to methods for obtaining peptides of SEQ ID No. 1 and SEQ ID No. 2. Whole casein is obtained from milk by acid precipitation and neutralization by means of an alkali according to well-known methods. For example, it is possible to use the NITSCHMANN and LEHMANN method (11). The casein or $\alpha_{s1}$-casein, used as a starting product for obtaining peptides according to SEQ ID No. 1 and SEQ ID No. 2, can be obtained by conventional methods well known to a person skilled in the art from milk, whole casein, caseinates and total protein concentrates of milk, obtained for example according to the methods described by THOMSON (12) and MAUBOIS (13). For example, it is possible to prepare $\alpha_{s1}$-casein by implementing the method described by SANOGO et al. (14). This method is a method of fractionation on DEAE-cellulose using a discontinuous gradient of calcium chloride as an eluent. It has the advantage of quickly separating all of the caseins. It can advantageously be implemented with, as an anion exchange support, the DEAE-cellulose DE 52 [sold by WHATMAN Ltd, Springfeld, Great Britain], which is a preconditioned resin not requiring any acid-basic pre-cycle before its first use. The peptides can then be obtained by hydrolysis of the casein with suitable enzymes. The peptides can then be concentrated or isolated by reverse-phase high-performance liquid chromatography (HPLC), by anion-exchange high-performance liquid chromatography or by gel filtration chromatography with a threshold of 1,000 Da or by membrane centrifugation and other membrane separation techniques (microfiltration, ultrafiltration, etc.).

The invention also therefore relates to a method for preparing peptides having a benzodiazepine-type activity and in particular an anxiolytic activity, characterized in that it includes the following steps:

enzymatic hydrolysis of the casein;
isolation of at least one peptide chosen from the peptides having SEQ ID Nos. 1 and 2.

By isolation, we mean the partial or total purification of the peptides or simply the enrichment of the hydrolysate obtained with peptides according to SEQ ID No. 1 and SEQ ID No. 2. This enrichment can be performed, for example, by fractionation of the hydrolysate obtained. Alternatively, the hydrolysate obtained from $\alpha_{s1}$-casein containing at least one peptide according to SEQ ID No. 1 or SEQ ID No. 2 can be used directly to obtain pharmaceutical compositions and food products according to the invention.

The peptides can also be obtained by peptide synthesis according to methods well known to a person skilled in the art, such as those described for example by MERIFFIELD (15).

The invention will now be described in greater detail with the following non-limiting examples.

FIGURES

FIG. 1: Elevated cross maze test
FIG. 2: Light/dark box test

EXAMPLES

Modalities for Obtaining the Pentapeptide

Whole casein is obtained from milk by acid precipitation and neutralization by means of an alkali according to well-known methods.

The pentapeptide having the following amino acid sequence: Tyr-Leu-Gly-Tyr-Leu identified by SEQ ID No: 1 with a molecular weight of 627 Da corresponds to $\alpha_{s1}$-casein peptide 91-95. It can be obtained from $\alpha_{s1}$-casein by enzymatic hydrolysis, in particular by means of trypsin and then pepsin. The hydrolysis of $\alpha_{s1}$-casein by trypsin releases various peptide fragments. The tryptic fragments are then together subjected to hydrolysis by pepsin A (EC 3.4.23.1) (obtained from porcine gastric mucous membrane, with an activity of 3,200-4,500 units/mg of protein), in a ratio E/S=1/200 at an acid pH, in a buffer and at an optimum room temperature for the enzyme activity for 240 minutes. This latter hydrolysis releases new fragments, including $\alpha_{s1}$-casein pentapeptide 91-95. This pentapeptide can also be generated from tryptic fragments of $\alpha_{s1}$-casein by hydrolysis by means of Corolase PP®, a mixture of pancreatic enzymes. The hydrolysis is performed for 240 minutes in a ratio E/S=1/100 at a pH, a temperature and in a buffer optimal for this enzymatic mixture. The pentapeptide can then be concentrated or isolated by reverse-phase high-performance liquid chromatography (HPLC), by anion-exchange high-performance liquid chromatography or by gel filtration chromatography or by membrane centrifugation and other membrane separation techniques (microfiltration, ultrafiltration, etc.).

Pharmaco-Behavioral Studies in the Wistar Rat

Elevated Cross Maze

Principle

The elevated cross maze test enables the density of the exploratory behavior in a new aversive situation to be measured [PELLOW et al., 1985 (16)]. The experiment exploits the conflict, in rodents, between the fear of open spaces and the desire to explore a new environment. The rat, placed at the center of the device, is forced to explore its environment. The open arms constitute an anxiety-producing environment, while this is not the case for the closed arms. The number of entries into all of the arms, the number of entries into the open arms, the number of entries into the closed arms, the time spent in the open arms, and the latency of entry into the first open arm constitute parameters reflecting the degree of anxiety of the animal.

Equipment

The elevated cross maze, made of wood, consists of four branches at 90° to one another. The two open branches (45×10 cm) and the two closed branches (45×10 cm, surrounded by wood plates over a height of 40 cm) are arranged opposite one another. The central square measures 10×10 cm. The open branches are illuminated by a white light with an intensity of 500 lx. The elevated cross maze is located 50 cm from the ground.

Protocol

The observations took place at between 9 and 11 o'clock in the morning in order to minimize the influence of the circadian rhythm. Before each passage through the elevated cross maze, the animal is placed for 10 minutes in an open field in order to stimulate its exploratory behavior. It is then placed in the central square of the elevated cross maze, and observed for 5 minutes. The cross maze is washed with 95% ethanol (v/v) between two passages so as to remove odors.

Treatments

The study involved 45 rats distributed among three groups:
a control group (15) rats having received 2 mL/kg of a solution containing 1% (v/v) glycerol and 0.2% (v/v) methylcellulose (vehicle),
a group treated with diazepam (Valium®, Roche, Neuilly-sur-Seine, France) at a dose of 1 mg/kg suspended in the vehicle (15 rats) serving as a positive control,
a group treated with $\alpha_{s1}$-casein fragment 91-95, pre-dissolved in the vehicle, at a dose of 0.5 mg/kg (15 rats).

The animals receive their respective treatment intraperitoneally one-half hour before being placed in the open field.

Results

The effect of the intraperitoneal injection in the Wistar rat of 2 mL/kg of a solution containing 1% (v/v) glycerol and 0.2% (v/v) methylcellulose (n=15) or 1 mg/kg of diazepam (n=15) or 0.5 mg/kg of pentapeptide CN$\alpha_{s1}$-f(91-95) (n=15) on (i) the total number of entries into the different arms, (ii) the number of entries into the open arms, and (iii) the time spent in the open arms was studied by non-parametric variance analysis (Kruskall-Wallis) and the comparisons of averages was performed by the Mann-Whitney test (A, B averages for each treatment significantly different p<0.05, FIG. 1). The exploratory activity of the animal, reflected by the number of entries into all of the arms, is not significantly different according to the treatment. The number of entries into the open arms and the time spent in the open arms of the animals treated with the vehicle are significantly lower than those of the animals treated with diazepam and those of the animals treated by $\alpha_{s1}$-casein fragment 91-95. No significant difference was observed between the diazepam and $\alpha_{s1}$-casein fragment 91-95. The $\alpha_{s1}$-casein fragment 91-95 has, in the elevated cross maze test in the Wistar rat, an action similar to that of diazepam, i.e. an increase in the exploration of anxiety-producing zones.

Light/Dark Box

Principle

The light/dark tests are based on the innate aversion of rodents for strongly illuminated environments and on their spontaneous exploratory behavior in response to mild stress factors such as a new environment and light. The light/dark box device enables the exploratory behavior of the rodent to be studied with regard to an unfamiliar aversive compartment (strongly illuminated with white light) after habituation in a non-aversive compartment (dark), which then becomes familiar [BOURIN and HASCOET, 2003 (17)]. Classic anxiolytics can be detected by using this device.

Equipment and Protocol

The light/dark box measures 65×49×35 cm (h×L×l) and is separated into two identical compartments by a plate with three 8×8-cm doors. The ground is covered with sawdust. Each rat is placed for 24 hours in the rear compartment of the box, and the doors communicating with the front compartment are made inaccessible. The rear compartment thus becomes the familiar compartment. The animal is fed and hydrated ad libitum. On the day of the test, the rat, after treatment, is again placed in the familiar compartment and the doors communicating with the front compartment (unfamiliar) are made accessible so that the animal can freely explore the environment. The unfamiliar compartment is made aversive by illumination with white light having an intensity of 1500 lx. The animals are observed for 10 minutes and the time spent in each of the compartments is measured.

Treatments

The study involved 36 rats distributed among three groups:
a control group (12 rats) having received 2 mL/kg of a solution containing 1% (v/v) glycerol and 0.2% (v/v) methylcellulose (vehicle),
a group treated with diazepam (Valium®, Roche, Neuilly-sur-Seine, France) at a dose of 1 mg/kg suspended in the vehicle (12 rats) serving as a positive control,
a group treated with $\alpha_{s1}$-casein fragment 91-95, pre-dissolved in the vehicle, at a dose of 0.5 mg/kg (12 rats).

The animals receive their respective treatments intraperitoneally one-half hour before the communication between the familiar compartment and the unfamiliar compartment is opened.

Results

Figure 2:
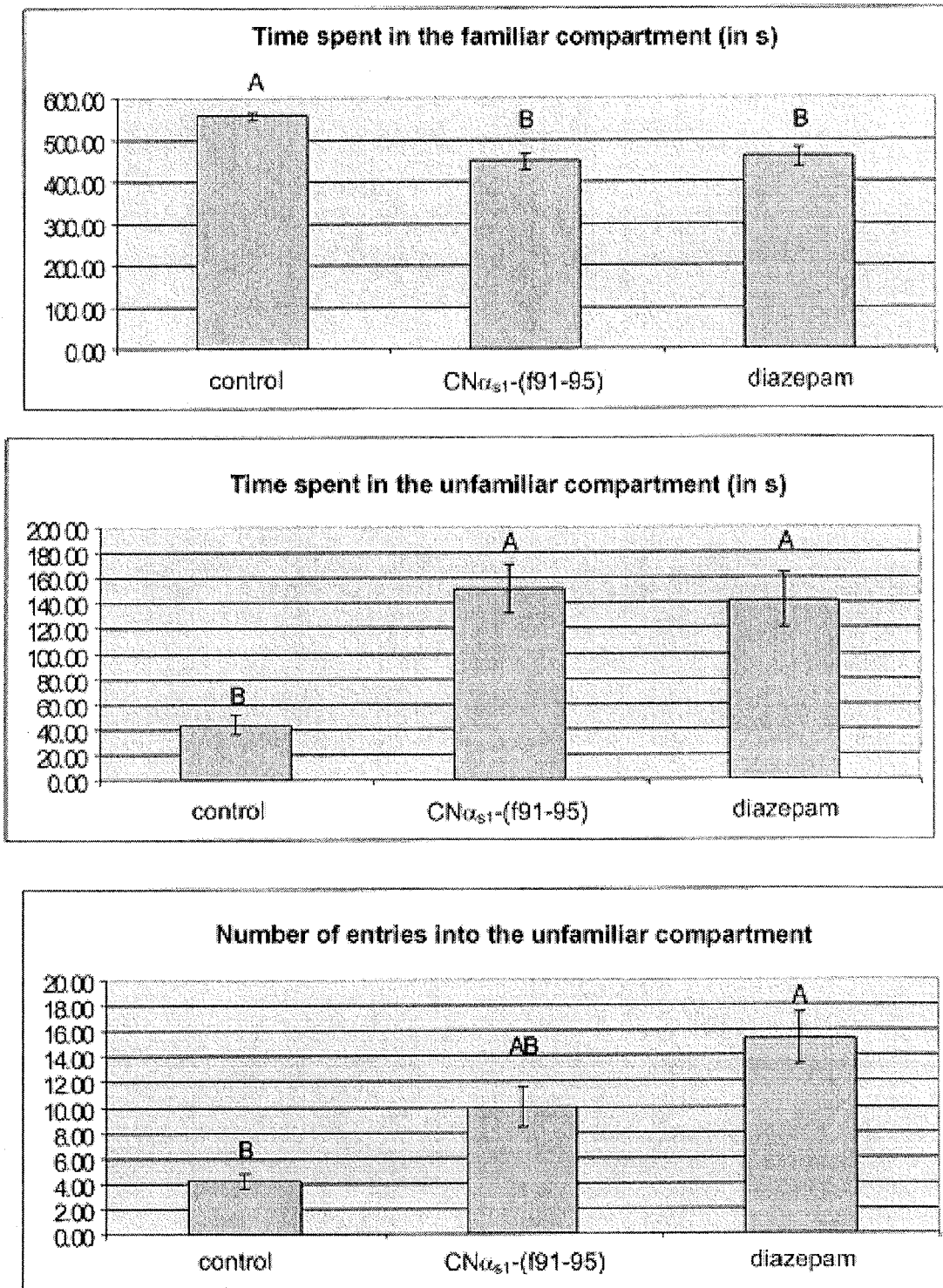

The effect of the intraperitoneal injection in the Wistar rat of 2 mL/kg of a solution containing 1% (v/v) glycerol and 0.2% (v/v) methylcellulose (n=12) or 1 mg/kg of diazepam (n=12) or 0.5 mg/kg of pentapeptide $CN\alpha_{s1}$-f(91-95) (n=12) on (i) the number of entries into the unfamiliar compartment, (ii) the time spent in the familiar compartment, and (iii) the time spent in the unfamiliar compartment was studied by non-parametric variance analysis (Kruskall-Wallis) and the comparisons of averages was performed by the Mann-Whitney test (A, B averages for each treatment significantly different $p<0.05$, FIG. 2). The time spent in the unfamiliar, aversive compartment by the animals treated with the vehicle is significantly lower than that of the animals treated with diazepam and that of the animals treated by $\alpha_{s1}$-casein fragment 91-95. Simultaneously, the time spent in the familiar compartment by the animals treated with the vehicle increases significantly. No significant difference was observed between the diazepam and $\alpha_{s1}$-casein fragment 91-95. The $\alpha_{s1}$-casein fragment 91-95 shows an anxiolytic-type action similar to that of diazepam in the light/dark box test in the Wistar rat.

BIBLIOGRAPHIC REFERENCES (1) MERCIER, J. C., GROSCLAUDE, F., and RIBADEAU-DUMAS, B., 1971, Structure primaire de la caséine $\alpha_{s1}$ bovine. Séquence complète. Eur. J. Biochem., 23, 41-51.
(2) NAGAO, M., MAKI, M., SASAKI, R., and CHIBA, H., 1984, Isolation and sequence analysis of bovine $\alpha_{s1}$-casein cDNA clone. Agric. Biol. Chem., 48, 1663-1667.
(3) ZIOUDROU, C., STREATY, R. A., and KLEE, W. A., 1979, Opioid peptides derived from food proteins; the exorophins. J. Biol. Chem., 254, 2446-2449.
(4) LOUKAS, S., VAROUCHA, D., ZIOUDROU, C., STREATY, R. A., and KLEE, W. A., 1983, Opioid activities and structure of α-casein-derived exorphins. Biochemistry, 22, 4567-4573.
(5) MARUYAMA, S., and SUZUKI, H., 1982, A peptide inhibitor of angiotensin I converting enzyme in the tryptic hydrolysate of casein. Agric. Biol. Chem., 46, 1393-1394.
(6) MARUYAMA, S., MITACHI, H., AWAYA, J., KURONO, M., TOMIZUKA, N., and SUZUKI, H., 1987, Angiotensin I-converting enzyme inhibitory activity of the C-terminal hexapeptide of $\alpha_{s1}$-casein. Agric. Biol. Chem., 51, 2557-2561.
(7) MICLO, L., PERRIN, E., DRIOU, A., BOUDIER, J.-F., IUNG, C., and LINDEN G., 1995, Utilisation d'un décapeptide à activité de type benzodiazépine pour la préparation de médicaments ed de compléments alimentaires. Brevet européen. Brevet européen no. EP 0714910A1.
(8) MICLO, L., PERRIN, E. DRIOU, A., PAPDOPOULOS, V., BOUJRAD, N., VANDERERSSE, R BOUDIER, J.-F., DESOR, D, LINDEN, G., and GAILLARD, J.-L., 2001, Characterization of α-casozepine, a tryptic peptide from bovine $\alpha_{s1}$-casein with benzodiazepine-like activity. FASEB J. (Jun. 8, 2001) 10.1096/fj.00-0685fje.
(9) LECOUVEY, M., FROCHOT, C., MICLO, L., ORLEWSKI, P., DRIOU, A., LINDEN, A., GAILLARD, J.-L., MARRAUD, M., CUNG, M.-T. and VANDERESSE R., 1997, Two dimensional $^1$H-NMR and CD structural analysis in a micellar medium of a bovine $\alpha_{s1}$-casein fragment having benzodiazepine-like properties. Eur. J. Biochem., 248, 872-878.
(10) FROCHOT, C. 1998, Etude d'un décapeptide à activité de type benzodiazépine issu d'une protéine du lait bovin. Thèse de l'Institut Polytechnique de Lorraine (INPL).
(11) NITSCHMANN, H. S., and LEHMANN, W., 1947, Zum Problem der Labwirkung auf Casein, Hely. Chim. Acta, 130, 804.
(12) THOMSON, A. R., 1984, Recent developments in protein recovery and purification. J. Chem. Tech. Biotechnol., 34B, 190-198.
(13) MAUBOIS, J. L., 1984. Separation, extraction and fractionation of milk protein components. Lait, 64, 485-495.
(14) SANOGO, T., PAQUET, D., AUBERT, F., and LINDEN, G., 1989, Purification of $\alpha_{s1}$-casein by Fast Protein Liquid Chromatography. J. Dairy Sci., 72, 2242-2246.
(15) MERRIFIELD, R. B., 1963, Solid phase peptide synthesis. I. Synthesis of a tetrapeptide. J. Am. Chem. Soc., 85, 2149-2154.
(16) PELLOW, S., CHOPIN, P., FILE, S. E., and BRILEY, M., 1985, Validation of open:closed arm entries in an elevated plus-maze as a measure of anxiety in the rat. J. Neurosci. Methods, 14, 149-167.
(17) BOURIN, M., and HASCOET, M., 2003, The mouse light/dark box test. Eur. J. Pharmacol., 463, 55-65.
(18) GUESDON et al., 2006, A tryptic hydrolysate from bovine milk alpha S1-casein improves sleep in rats subjected to chronic mild stress, 27:6, 1476-1482.

The invention claimed is:

1. A method of treating anxiety, sleep disorders and epilepsy comprising administering a composition comprising an effective amount of at least one peptide consisting of the sequence SEQ ID No: 1 or SEQ ID No: 2.

2. A method of treating anxiety, sleep disorders and epilepsy comprising administering a composition comprising a hydrolysate of casein $\alpha_{s1}$-casein and/or a fraction of a hydrolysate of casein or $\alpha_{s1}$-casein, containing an effective amount of at least one peptide consisting of the sequence SEQ ID No: 1 or SEQ ID No: 2.

3. The method of claim 1, wherein the method treats anxiety.

4. The method of claim 1, wherein the method treats sleep disorders.

5. The method of claim 1, wherein the method treats epilepsy.

6. The method of claim 1, wherein the peptide is produced by a recombinant organism.

7. The method of claim 6, wherein the recombinant organism is selected from the group consisting of bacteria, yeast and a mammalian cell.

8. The method of claim 2, wherein the method treats anxiety.

9. The method of claim 2, wherein the method treats sleep disorders.

10. The method of claim 2, wherein the method treats epilepsy.

11. The method of claim 2, wherein the peptide is produced by a recombinant organism.

12. The method of claim 11, wherein the recombinant organism is selected from the group consisting of bacteria, yeast and a mammalian cell.

* * * * *

UNITED STATES PATENT AND TRADEMARK OFFICE
CERTIFICATE OF CORRECTION

PATENT NO. : 8,530,423 B2
APPLICATION NO. : 12/996506
DATED : September 10, 2013
INVENTOR(S) : Federique Balandras et al.

Page 1 of 1

It is certified that error appears in the above-identified patent and that said Letters Patent is hereby corrected as shown below:

In the claims:

Claim 2, column 11, line 18, "hydrolysate of casein" should be changed to --hydrolysate of casein or--

Signed and Sealed this
Twelfth Day of November, 2013

Teresa Stanek Rea
*Deputy Director of the United States Patent and Trademark Office*